US012279791B2

United States Patent
McFarland (10) Patent No.: US 12,279,791 B2
(45) Date of Patent: Apr. 22, 2025

(54) METHOD OF PERFORMING A MINIMIALLY INVASIVE CARPAL TUNNEL RELEASE USING AN INTERVENTIONAL RADIOLOGY PROCEDURE

(71) Applicant: Robert McFarland, Wichita, KS (US)

(72) Inventor: Robert McFarland, Wichita, KS (US)

( * ) Notice: Subject to any disclaimer, the term of this patent is extended or adjusted under 35 U.S.C. 154(b) by 742 days.

(21) Appl. No.: 17/455,837

(22) Filed: Nov. 19, 2021

(65) Prior Publication Data

US 2022/0096117 A1    Mar. 31, 2022

Related U.S. Application Data

(63) Continuation of application No. PCT/US2020/035894, filed on Jun. 3, 2020.

(60) Provisional application No. 62/856,616, filed on Jun. 3, 2019.

(51) Int. Cl.
*A61B 17/34*   (2006.01)
*A61B 17/32*   (2006.01)

(52) U.S. Cl.
CPC .. *A61B 17/3403* (2013.01); *A61B 17/320036* (2013.01); *A61B 2017/3413* (2013.01); *A61B 2017/3454* (2013.01)

(58) Field of Classification Search
CPC ..... A61B 17/32; A61B 17/34; A61B 17/3403; A61B 17/320036; A61B 2017/3454; A61B 2017/3413
See application file for complete search history.

(56) References Cited

U.S. PATENT DOCUMENTS

| RE33,258 E | 7/1990 | Onik et al. |
| 7,004,927 B2* | 2/2006 | Ferguson ............ A61M 5/3275 604/110 |
| 2006/0173377 A1 | 8/2006 | Mccullough |
| 2012/0029542 A1* | 2/2012 | Huang ........... A61B 17/320036 606/167 |
| 2013/0310750 A1 | 11/2013 | Hopman |
| 2014/0121456 A1 | 5/2014 | McCormack et al. |
| 2015/0342756 A1 | 12/2015 | Bays |
| 2017/0281214 A1* | 10/2017 | Brown ............... A61B 17/3496 |

FOREIGN PATENT DOCUMENTS

| CN | 107708783 A | 2/2018 |
| EP | 0704189 A1 | 4/1996 |
| WO | 2016176403 A1 | 11/2016 |

OTHER PUBLICATIONS

Extended Search Report of the European Patent Office in EP Application No. 20819595.8, dated Jan. 4, 2023; 7pgs.

(Continued)

*Primary Examiner* — Vi X Nguyen
(74) *Attorney, Agent, or Firm* — Stinson LLP (57) ABSTRACT

The present disclosure provides a method of performing an image guided carpal tunnel release procedure. The method includes directing fluid through a hypodermic needle toward a median nerve of a patient to move the median nerve away from a deep surface of a transverse carpal ligament (TCL) of the patient. The method further includes dissecting the TCL with the hypodermic needle by sliding a cutting edge associated with the hypodermic needle along the TCL.

24 Claims, 10 Drawing Sheets

(56) References Cited

OTHER PUBLICATIONS

Mcshane et al. Sonographically Guided Percutaneous Needle Release of the Carpal Tunnel for Treatment of Carpal Tunnel Syndome. Journal of Ultrasound in Medicine 31(9): 1341-1349, 2012 [retrieved on Jan. 8, 2020]. Retrieved from the Internet <URL: https://onlinelibrary.wiley.com/doi/pdf/10.7863/jum.2012.31.9.1341> entire document.

International Search Report and Written Opinion, dated Aug. 28, 2020. 10 pages.

\* cited by examiner

METHOD OF PERFORMING A MINIMIALLY INVASIVE CARPAL TUNNEL RELEASE USING AN INTERVENTIONAL RADIOLOGY PROCEDURE

CROSS-REFERENCE TO RELATED APPLICATION

This application claims priority to U.S. Provisional Patent Application No. 62/856,616, filed Jun. 3, 2019, and entitled METHOD OF PERFORMING A MINIMALLY INVASIVE CARPAL TUNNEL RELEASE USING AN INTERVENTIONAL RADIOLOGY PROCEDURE, which is hereby incorporated by reference in its entirety.

FIELD

The present disclosure generally relates to a method of performing a carpal tunnel release, and more specifically, to a method of performing a minimally invasive carpal tunnel release using an interventional radiology procedure.

BACKGROUND

Interventional radiology is a radiology specialty in which minimally invasive procedures are performed using image guidance. Interventional radiology procedures may be performed for a variety of reasons. For example, some interventional radiology procedures are done for diagnostic purposes (e.g., biopsy). Other interventional radiology procedures are performed for treatment purposes (e.g., radiofrequency ablation).

During an interventional radiology procedure, a radiologist uses images as guidance for operating with medical instruments. Common interventional imaging methods include, for example, X-ray fluoroscopy, computed tomography, ultrasound, and magnetic resonance imaging (MRI). Medical instruments used in interventional radiology procedures typically include, for example, needles, catheters, drains, and guidewires. The medical instruments are inserted into a patient's body through skin, through a body cavity, or through an anatomical opening. The use of an imaging method allows the radiologist to guide these medical instruments through the body to a specific area of interest.

Figure 1:
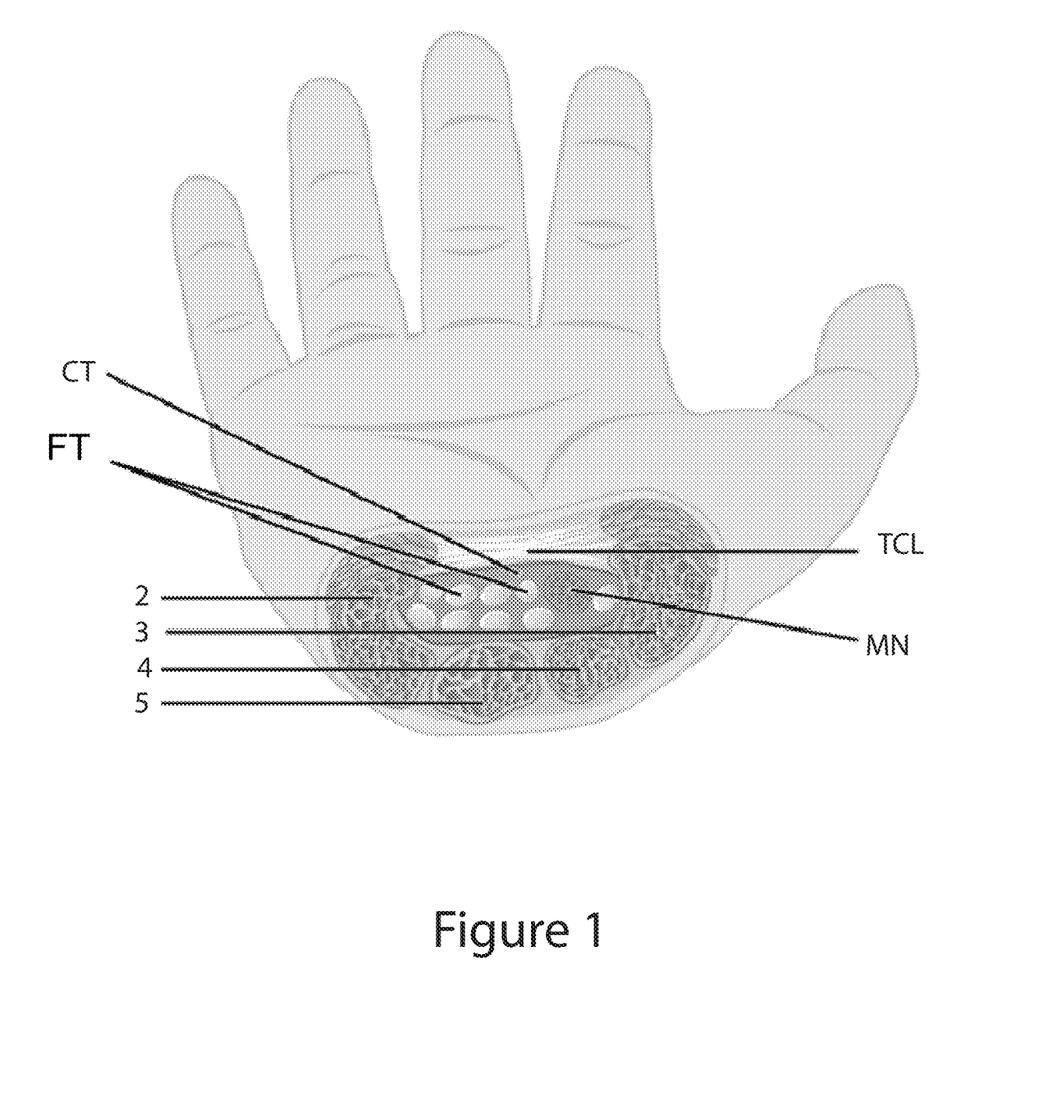
FIG. 1 is an image of a patient's wrist showing anatomical structures relevant to carpal tunnel syndrome.

A common condition associated with the hands/wrists of a patient is carpal tunnel syndrome. Carpal tunnel syndrome is a common neuropathy. In fact, it is one of the most common nerve compression syndromes. The carpal tunnel (CT) is illustrated in FIG. 1. Carpal tunnel syndrome involves compression of a patient's median nerve (MN) deep in the wrist. Most commonly, the patient's median nerve MN is compressed by the transverse carpal ligament (TCL) (also referred to as the flexor retinaculum). The TCL attaches to the hook of hamate (labeled as element 2) and the trapezium (labeled as element 3). The TCL forms the roof of the carpal tunnel located on the volar aspect of the wrist. As seen in FIG. 1, the median nerve is deep to the TCL. Other anatomical elements are the flexor tendons FT, trapezoid (labeled as element 4), and the capitate (labeled as element 5). The image shown in FIG. 1 is adapted from "Anatomy and Physiology," May 2, 2019 Openstax, available for free download at http://cnx.org/contents/ccc4ed14-6c87-408b-9934-7a0d249d853@8. Other potential causes for the compression of the patient's median nerve MN other than the TCL are space occupying lesions (e.g., ganglion cysts).

Most often, a patient experiencing carpal tunnel syndrome is prescribed nonsurgical methods in an attempt to remediate the compression of the median nerve. These nonsurgical methods may include rest, splinting, physical therapy, and corticosteroid injections. If one or more of the aforementioned nonsurgical methods fails to remediate the compression of the median nerve MN, a release of the median nerve MN may be achieved by sectioning the TCL.

Historically, the TCL has been sectioned using open surgery. Open carpal tunnel releases, however, have a number of drawbacks. For example, open surgery is invasive and requires a large incision (often times more than 60 mm in length). The large incision increases scarring, the risk of infection, and the risk of complication during the surgery. It also increases the recovery period for a patient. Additionally, an open carpal tunnel release must be performed in an operating room and requires multiple specialists to be present (e.g., an orthopedic surgeon and an anesthesiologist). The necessity to perform an open carpal tunnel release in an operating room with multiple specialists present dramatically increases medical costs associated with the procedure.

Accordingly, there is a need for a new method of performing a carpal tunnel release using interventional radiology procedures so that the carpal tunnel release is minimally invasive and capable of being performed during an office visit at an outpatient facility. Such a method would not only decrease the risks of scarring and infection associated with carpal tunnel releases, but it would also reduce patient recovery time and overall medical costs.

SUMMARY

In one aspect, a method of performing an interventional radiology procedure on a patient exhibiting symptoms of carpal tunnel syndrome in an affected wrist comprises orienting the affected wrist of the patient in a palmar position. A hypodermic needle is guided through a wrist crease of the affected wrist to a position immediately superficial of the transverse carpal ligament (TCL). The hypodermic needle has a hypodermic needle bore and a sharpened distal tip. Fluid is at least intermittently injected through the hypodermic needle bore while the hypodermic needle is guided to the position immediately superficial of the TCL. The sharpened distal tip of the hypodermic needle is pieced through the TCL while injecting fluid. The fluid pushes the median nerve away from the TCL and provides a fluid pocket. The fluid pocket isolates the median nerve. The hypodermic needle is oriented such that at least a portion of the sharpened distal tip is in contact with the TCL. The TCL is dissected with the sharpened distal tip by moving the hypodermic needle in a reciprocating motion. The reciprocating motion causes the sharpened distal tip to wear against the TCL until said TCL is dissected. The interventional radiology procedure is performed under continuous imaging, thereby enabling anatomic structures of the affected wrist to be visualized throughout the procedure.

In another aspect, a method of performing an image guided carpal tunnel release procedure comprises directing fluid through a hypodermic needle toward a median nerve of a patient to move the median nerve away from a deep surface of a transverse carpal ligament (TCL) of the patient. Subsequently the TCL is dissected with the hypodermic needle by sliding a cutting edge associated with the hypodermic needle along the TCL.

In another aspect, a method of performing an image guided carpal tunnel release procedure comprises directing a first fluid through a needle bore of the hypodermic needle to move a median nerve of a patient to create clearance for dissecting a transverse carpal ligament (TCL) of the patient.

After the clearance is created, the TCL is dissected using at least one of the hypodermic needle and an implement passed through the bore of the hypodermic needle. A second fluid comprising a steroid is directed through the needle bore toward the dissected TCL.

Other aspects will be in part apparent and in part pointed out hereinafter.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter.

DETAILED DESCRIPTION

The present disclosure provides a method for performing a minimally invasive carpal tunnel release using an interventional radiology procedure. The method aims to alleviate the symptoms experienced by a patient having a hand/wrist affected by carpal tunnel syndrome without undergoing open surgery. The method described herein enables a radiologist to maintain direct visualization of the patient's affected wrist throughout the entirety of the carpal tunnel release procedure. Direct visualization ensures the radiologist can guide the instrument(s) being used during the procedure to the necessary location within the patient without damaging any nerves and/or blood vessels. Although this disclosure describes certain exemplary methods of performing carpal tunnel release as being conducted by a radiologist, it is to be understood that other practitioners or medical health professionals could conduct one or more aspects of any of the methods described herein.

Direct visualization can be achieved through several different types of interventional imaging methods, including, for example, X-ray fluoroscopy, computed tomography, ultrasound, and magnetic resonance imaging (MRI). The imaging method discussed throughout the remaining portion of the detailed description will be ultrasound. A person of ordinary skill in the art will understand, however, that other suitable imaging methods could be used in accordance with the method disclosed herein.

Figure 2:
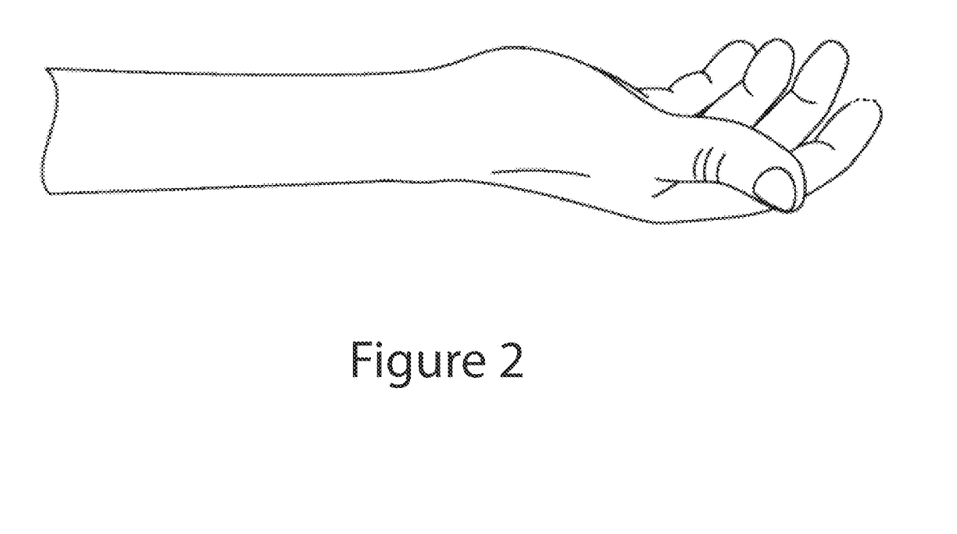
FIG. 2 is a side view illustration of an affected wrist in a palmar position.
Figure 3:
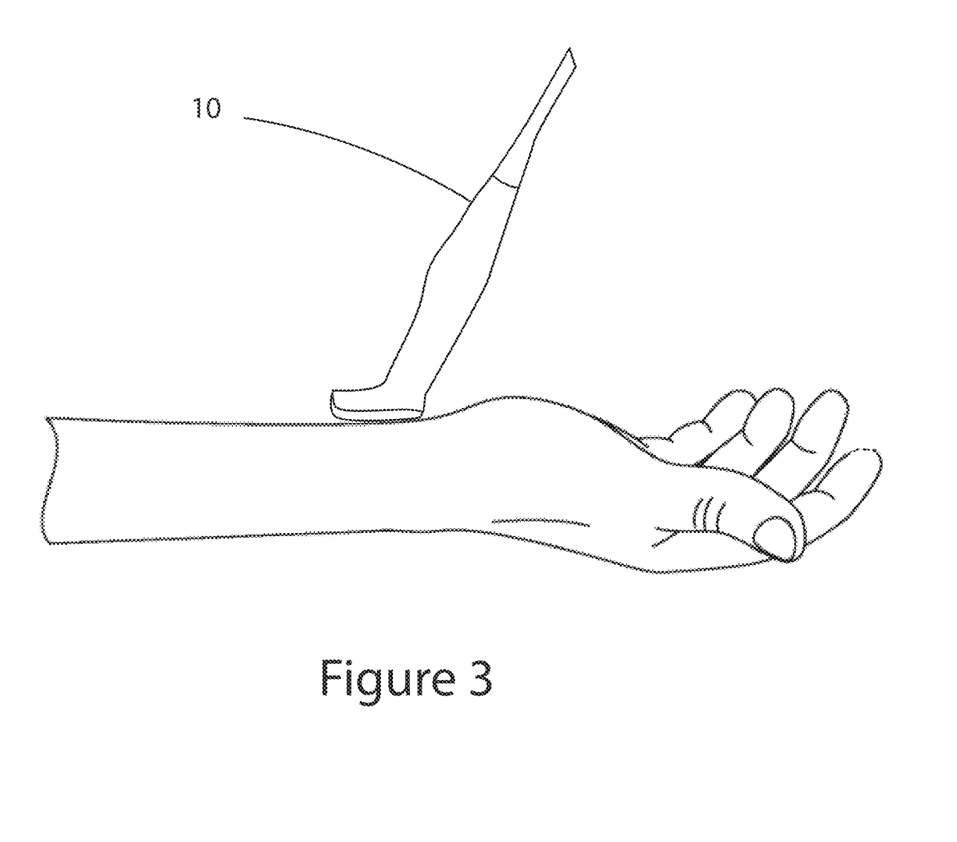
FIG. 3 is a side view illustration of the affected wrist shown in FIG. 2 with an ultrasound transducer positioned on the wrist.
Figure 4:
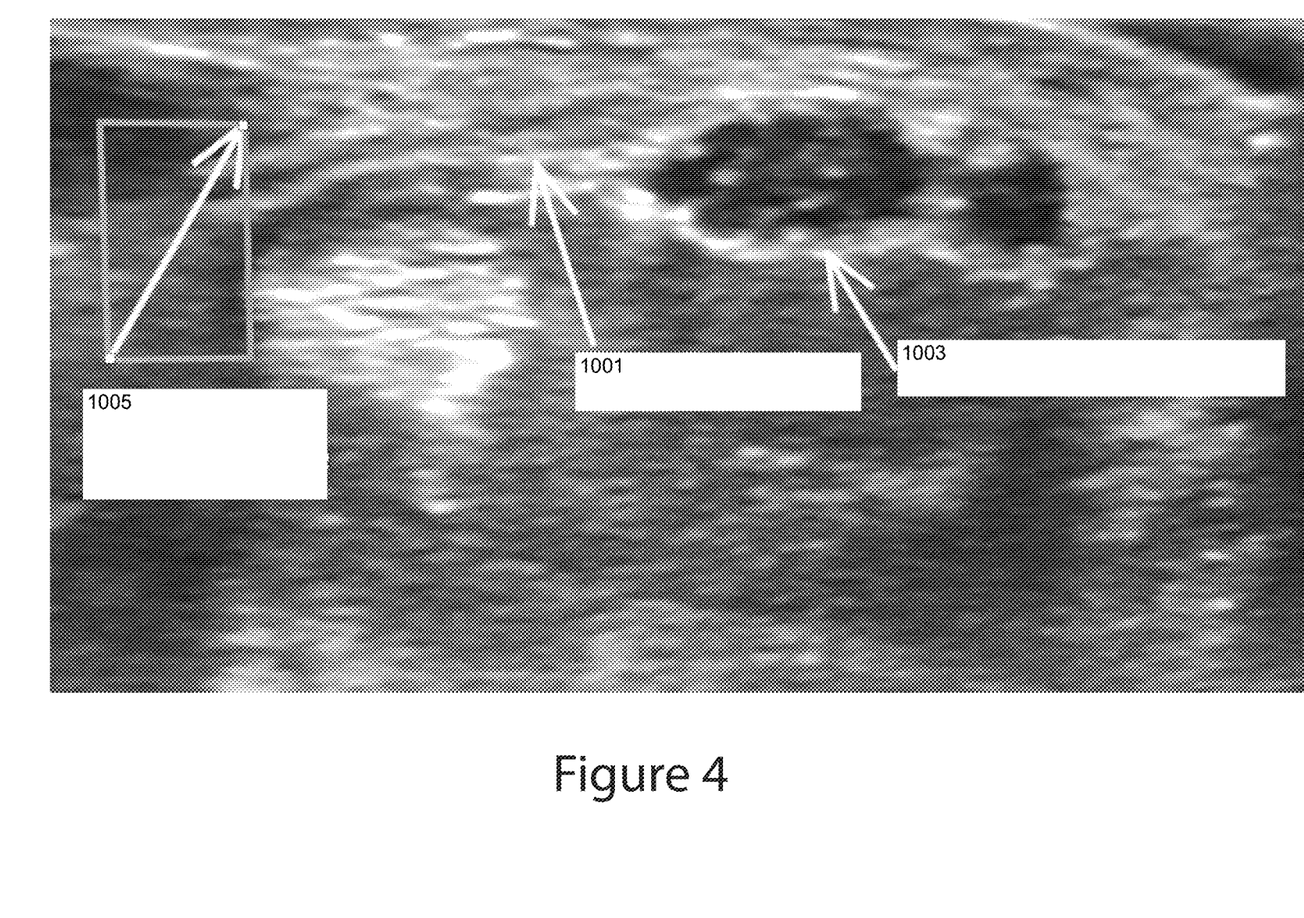
FIG. 4 is an ultrasound image showing anatomical structures relevant to carpal tunnel syndrome.

At the beginning of the interventional radiology procedure, the patient is placed in a supine position or a recumbent position, depending upon the circumstances. For example, a radiologist may prefer to place the patient in either a supine position or a sitting position depending upon available room equipment (e.g., bed or chair) and room layout. The patient's affected wrist is oriented such that the palm correlating to the affected wrist is facing upwards (i.e., palmar), as illustrated in FIG. 2. An ultrasound transducer 10 is placed on a palmar side of the patient's wrist, as illustrated in FIG. 3, to enable the radiologist to determine the cross-sectional anatomy of the patient's wrist. A person of ordinary skill in the art will understand that the probe may be placed longitudinally on the patient's wrist or transversely, depending upon the imaging desired by the radiologist. Preferably, the ultrasound transducer is a high frequency transducer (e.g., 15-7 MHz transducer). For example, the ultrasound transducer may be a high frequency, small footprint linear array transducer (commonly referred to as a "hockey stick" transducer). One such type of an ultrasound transducer is Philips L15-7io broadband compact linear array transducer. It is to be understood that the radiologist could be holding and maneuvering the ultrasound transducer with one hand throughout the procedure, enabling the radiologist to hold and maneuver an instrument comprising a hypodermic needle (e.g., a syringe connected to the hypodermic needle) in the opposite hand. Alternatively, an assistant (e.g., nurse or radiology technologist) could be handling and maneuvering the ultrasound transducer throughout the procedure. As can be seen in the ultrasound image shown in FIG. 4, some of the primary anatomical structures to be viewed by the radiologist are: (i) TCL (labeled as 1001 in the image); (ii) muscle tendons; and the (iii) median nerve (labeled as 1003). In the ultrasound image shown in FIG. 4, a portion of a hypodermic needle (labeled as 1005) being introduced into the patient can be seen.

Figure 5:
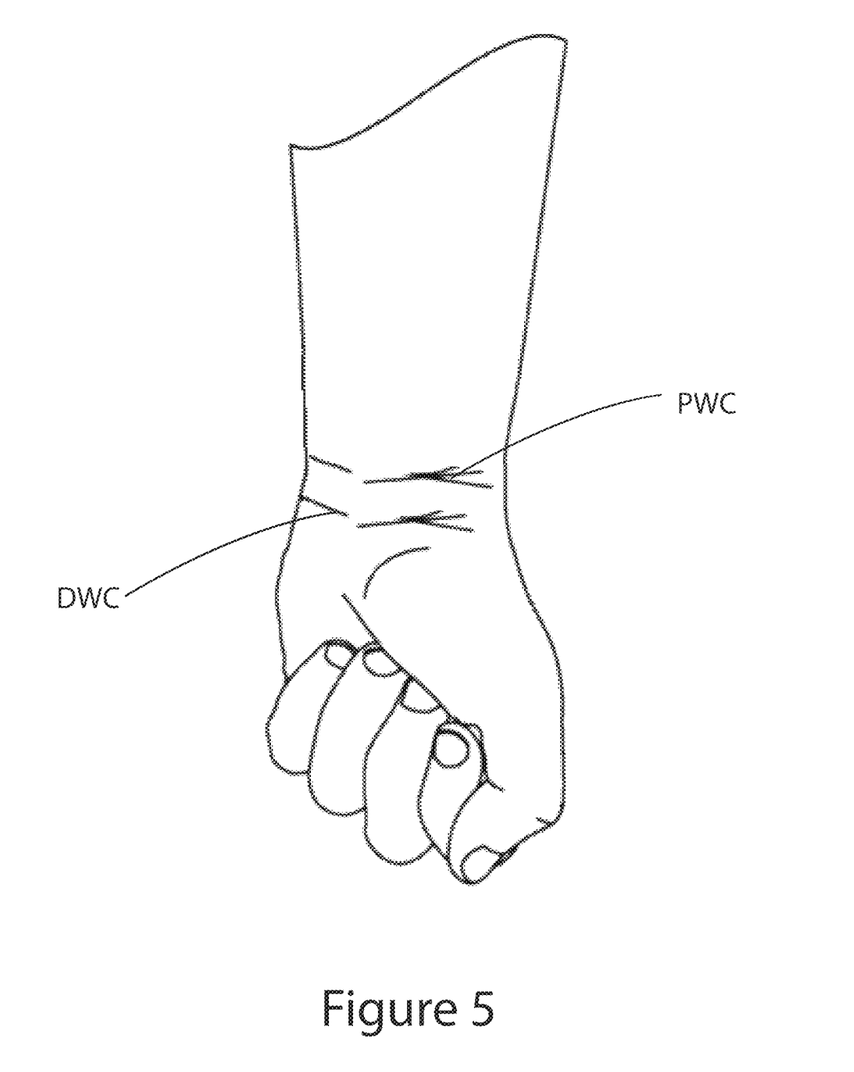
FIG. 5 is a top view illustration of the affected wrist shown in FIG. 2, the affected writing being oriented in the palmar position.

After the radiologist visualizes the anatomical structures of the patient's affected wrist, a first hypodermic needle (referred to from hereon as the "numbing needle") may be introduced through a wrist crease of the affected wrist. The wrist crease can be either the proximal wrist crease PWC or the distal wrist crease DWC, as illustrated in FIG. 5. A fluid fitting (e.g., a Luer lock) may be connected to a proximal end of the numbing needle. The fluid fitting enables a syringe containing numbing fluid to be fluidly connected with the numbing needle. A person of ordinary skill in the art will understand that the numbing fluid may contain, for example, a mixture of saline, lidocaine, and/or triamcinolone acetonide. The numbing fluid serves the purpose of numbing the patient's affected anatomy to ensure the patient will remain still during the interventional radiology procedure and to ensure the patient's comfort during the procedure. A person of ordinary skill in the art will understand that the numbing needle may be a small needle because the numbing needle is the first hypodermic needle introduced into the patient. The numbing needle may be introduced at an acute angle to the skin surface. A person of ordinary skill in the art will understand that the numbing needle could be introduced at an angle perpendicular to the skin surface. Under ultrasonographic guidance, the numbing needle is guided to a deep surface of the TCL while ensuring that a distal end of the hypodermic needle does not engage or contact the median nerve. Depending on the circumstances, the radiologist may elect not to pierce the TCL (i.e., remain on the superficial surface of the TCL) with the numbing needle. A person of ordinary skill in the art will understand that the numbing needle may be introduced into the patient proximal-to-distal relative to the affected wrist (shown in FIG. 6) or distal-to-proximal relative to the affected wrist (shown in FIG. 7). The numbing fluid is at least intermittently injected through the numbing needle as the numbing needle is guided to the TCL.

After the patient is sufficiently anesthetized, the radiologist removes the numbing needle from the patient and introduces a second hypodermic needle (referred to hereon as the "procedure needle") into the patient. The procedure needle is used during the interventional radiology procedure to perform the carpal tunnel release. For this reason, the procedure needle will likely be larger in size than the numbing needle. Other than differing in size, the procedure needle can be substantially similar to the numbing needle. In one embodiment, the numbing needle and the procedure needle are configured to conform to a size defined by the Birmingham gauge. The Birmingham gauge is a system used to specify thickness and/or diameter of hypodermic needles (i.e., needles that enter the skin). The Birmingham gauge is also known as the Birmingham wire gauge. The following table provides nominal outer diameter, nominal inner diameter, and nominal wall thickness for hypodermic needles defined by the Birmingham gauge. The nominal inner diameters and nominal wall thicknesses of the various gauges may vary from the dimensions shown below.

| | Needle | | | | | |
|---|---|---|---|---|---|---|
| | Nominal outer diameter | | Nominal inner diameter | | Nominal wall thickness | |
| Gauge | Mm | tolerance (mm) | mm | tolerance (mm) | mm | tolerance (mm) |
| 7 | 4.572 | ±0.025 | 3.810 | ±0.076 | 0.381 | ±0.025 |
| 8 | 4.191 | ±0.025 | 3.429 | ±0.076 | 0.381 | ±0.025 |
| 9 | 3.759 | ±0.025 | 2.997 | ±0.076 | 0.381 | ±0.025 |
| 10 | 3.404 | ±0.025 | 2.692 | ±0.076 | 0.356 | ±0.025 |
| 11 | 3.048 | ±0.025 | 2.388 | ±0.076 | 0.330 | ±0.025 |
| 12 | 2.769 | ±0.025 | 2.159 | ±0.076 | 0.305 | ±0.025 |
| 13 | 2.413 | ±0.025 | 1.803 | ±0.076 | 0.305 | ±0.025 |
| 14 | 2.108 | ±0.025 | 1.600 | ±0.076 | 0.254 | ±0.025 |
| 15 | 1.829 | ±0.013 | 1.372 | ±0.038 | 0.229 | ±0.013 |
| 16 | 1.651 | ±0.013 | 1.194 | ±0.038 | 0.229 | ±0.013 |

-continued

| | Needle | | | | | |
|---|---|---|---|---|---|---|
| | Nominal outer diameter | | Nominal inner diameter | | Nominal wall thickness | |
| Gauge | Mm | tolerance (mm) | mm | tolerance (mm) | mm | tolerance (mm) |
| 17 | 1.473 | ±0.013 | 1.067 | ±0.038 | 0.203 | ±0.013 |
| 18 | 1.270 | ±0.013 | 0.838 | ±0.038 | 0.216 | ±0.013 |
| 19 | 1.067 | ±0.013 | 0.686 | ±0.038 | 0.191 | ±0.013 |
| 20 | 0.9081 | ±0.0064 | 0.603 | ±0.019 | 0.1524 | ±0.0064 |
| 21 | 0.8192 | ±0.0064 | 0.514 | ±0.019 | 0.1524 | ±0.0064 |
| 22 | 0.7176 | ±0.0064 | 0.413 | ±0.019 | 0.1524 | ±0.0064 |
| 22s | 0.7176 | ±0.0064 | 0.152 | ±0.019 | 0.2826 | ±0.0064 |
| 23 | 0.6414 | ±0.0064 | 0.337 | ±0.019 | 0.1524 | ±0.0064 |
| 24 | 0.5652 | ±0.0064 | 0.311 | ±0.019 | 0.1270 | ±0.0064 |
| 25 | 0.5144 | ±0.0064 | 0.260 | ±0.019 | 0.1270 | ±0.0064 |
| 26 | 0.4636 | ±0.0064 | 0.260 | ±0.019 | 0.1016 | ±0.0064 |
| 26s | 0.4737 | ±0.0064 | 0.127 | ±0.019 | 0.1734 | ±0.0064 |
| 27 | 0.4128 | ±0.0064 | 0.210 | ±0.019 | 0.1016 | ±0.0064 |
| 28 | 0.3620 | ±0.0064 | 0.184 | ±0.019 | 0.0889 | ±0.0064 |
| 29 | 0.3366 | ±0.0064 | 0.184 | ±0.019 | 0.0762 | ±0.0064 |
| 30 | 0.3112 | ±0.0064 | 0.159 | ±0.019 | 0.0762 | ±0.0064 |
| 31 | 0.2604 | ±0.0064 | 0.133 | ±0.019 | 0.0635 | ±0.0064 |
| 32 | 0.2350 | ±0.0064 | 0.108 | ±0.019 | 0.0635 | ±0.0064 |

In a preferred embodiment of performing the method disclosed herein, the numbing needle is a 23-gauge hypodermic needle or greater on the Birmingham gauge. For example, the numbing needle has an outer diameter of less than or equal to about 0.75 mm in one or more embodiments (e.g., less than or equal to about 0.70 mm, less than or equal to 0.65 mm). In an exemplary embodiment, the procedure needle has a gauge number on the Birmingham gauge of less than or equal to 21. For example, the procedure needle has an outer diameter of at least about 0.75 mm in one or more embodiments (e.g., at least about 0.80 mm). Using a larger needle for the procedure needle may provide the radiologist a larger, more robust instrument to perform the carpal tunnel release, as described in more detail below. Suitably, however, the procedure needle is also sufficiently small in cross-sectional size to navigate the carpal tunnel anatomy under ultrasound guidance without inadvertently damaging, for example, nerves or blood vessels. In one or more embodiments, the procedure needle has an outer diameter of less than or equal to 2.5 mm (e.g., less than or equal to about 2.0 mm, less than or equal to about 1.7 mm, less than or equal to about 1.5 mm, less than or equal to about 1.4 mm). In one or more embodiments, the procedure needle comprises one of a 16-gauge, 17-gauge, 18-gauge, 19-gauge, 20-gauge, 21-gauge, and 22-gauge needle on the Birmingham gauge or otherwise comprises a needle of comparable external cross-sectional size to any in this group or any subset of this group of Birmingham needles. A person of ordinary skill in the art will understand that the procedure needle could be used to perform the anesthetization in lieu of the numbing needle.

Figure 8:
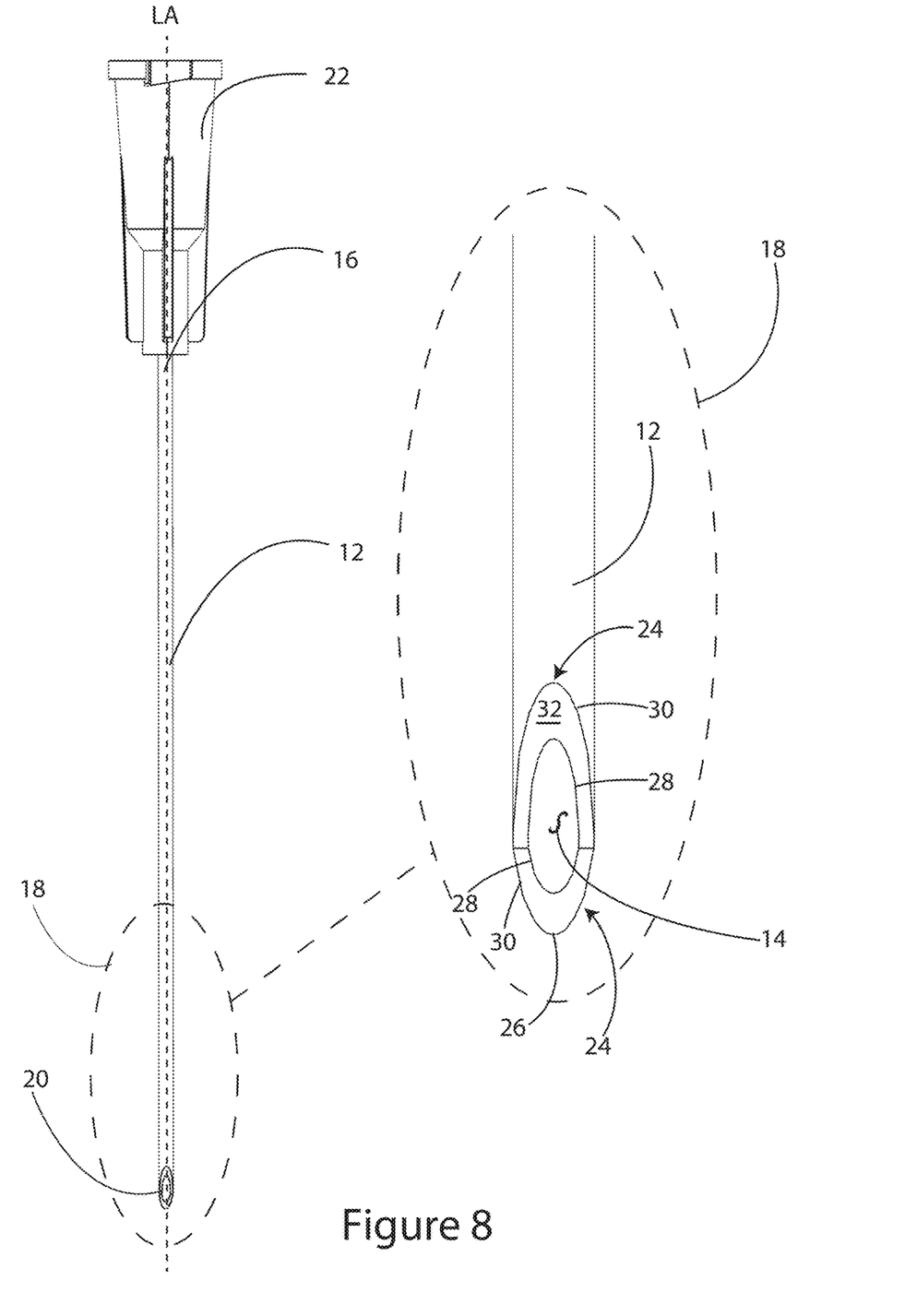
FIG. 8 is a front view illustration of a generic hypodermic needle, the illustration including a magnified view of a distal end of the hypodermic needle.
Figure 9:
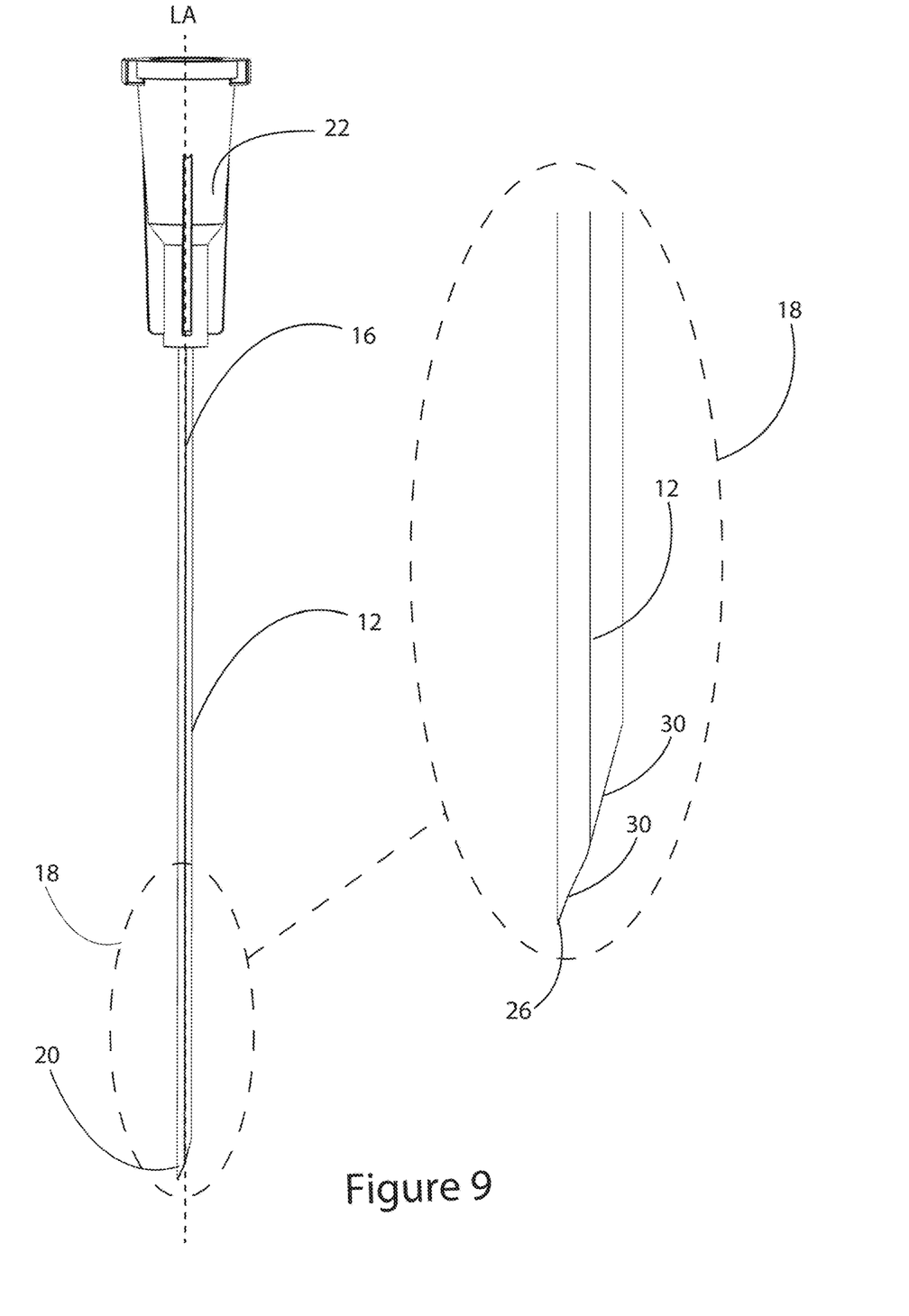
FIG. 9 is a side view illustration of the generic hypodermic needle, the illustration including a magnified view of the distal end of the hypodermic needle.
Figure 10:
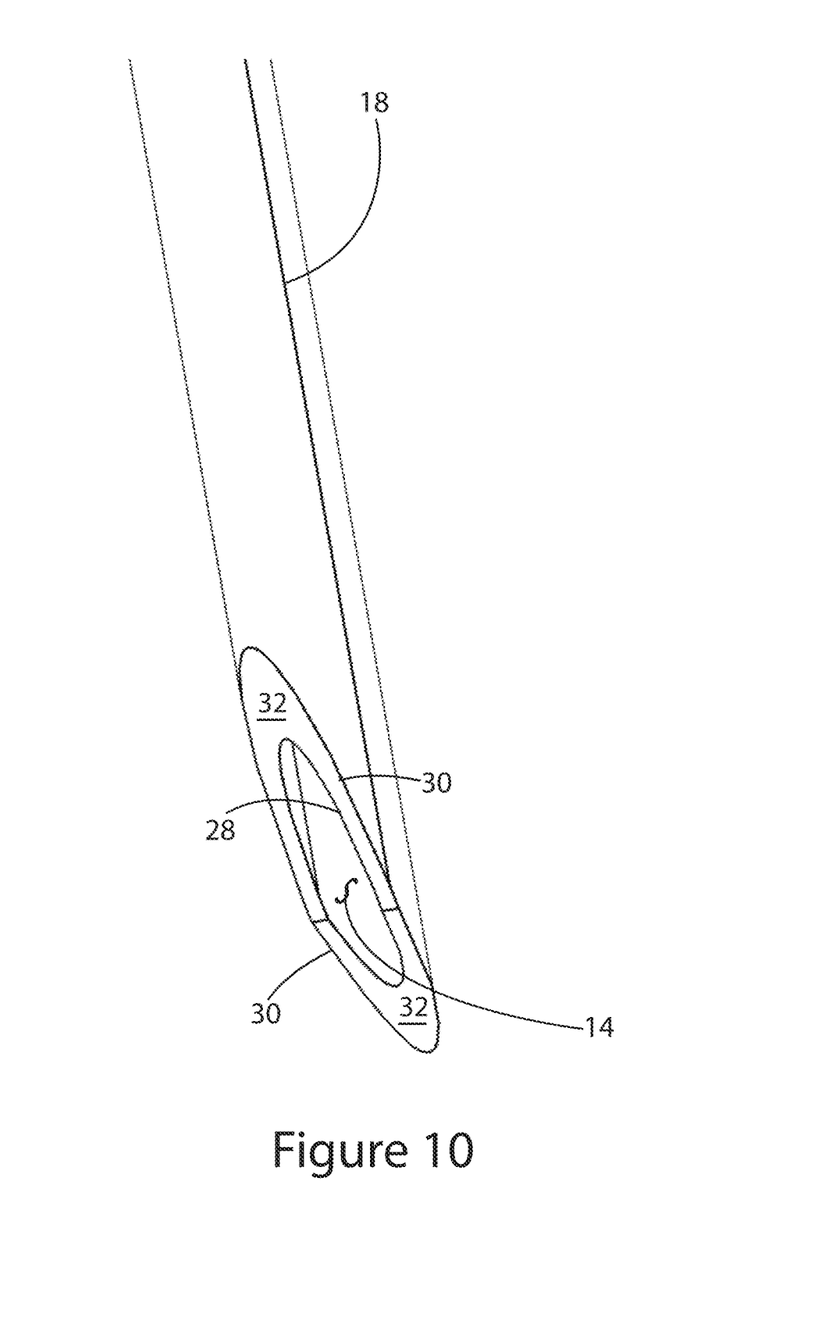
FIG. 10 is a perspective view illustration of the distal end of the generic hypodermic needle shown in FIGS. 8-9.

As seen in FIGS. 8-10, the procedure needle includes a shaft 12, a bore 14 extending from a proximal end 16 to a distal end 18, a sharpened distal tip 20, and a longitudinal axis LA. The shaft 12 extends longitudinally along the longitudinal axis LA. A fluid fitting 22 (e.g., a Luer lock) may be connected to the proximal end 16 of the procedure needle. The fluid fitting 22 enables a syringe containing fluid to be fluidly connected with the procedure needle. A person of ordinary skill in the art will understand that the fluid may be saline because the patient has already been anesthetized. Alternatively, the fluid may be a numbing fluid containing, for example, a mixture of saline, lidocaine, and/or triamcinolone acetonide. The sharpened distal tip 20 includes at least one bevel 24 and a point 26. A person of ordinary skill in the art will understand that, depending on the hypodermic needle design being used as the procedure needle, the sharpened distal tip may include more than one bevel. For example, the hypodermic needle shown in FIGS. 8-10 has two bevels. Other designs include up to five bevels. As seen in FIGS. 8-10, each bevel 24 includes an inner bevel edge 28 and an outer bevel edge 30. The inner bevel edge 28 at least partially defines the bore 14 of the procedure needle. The outer bevel edge 30 is spaced from the inner bevel edge 28 by a bevel surface 32. In the embodiment shown in FIGS. 8-10, the bevel surface 32 comprises two generally planar surface portions. A person of ordinary skill in the art will understand that the procedure needle could be manufactured from a metal material (e.g., stainless steel, titanium, Nitinol, or tungsten carbide) or a ceramic material (e.g., zirconia, alumina, or sapphire).

Figure 6:
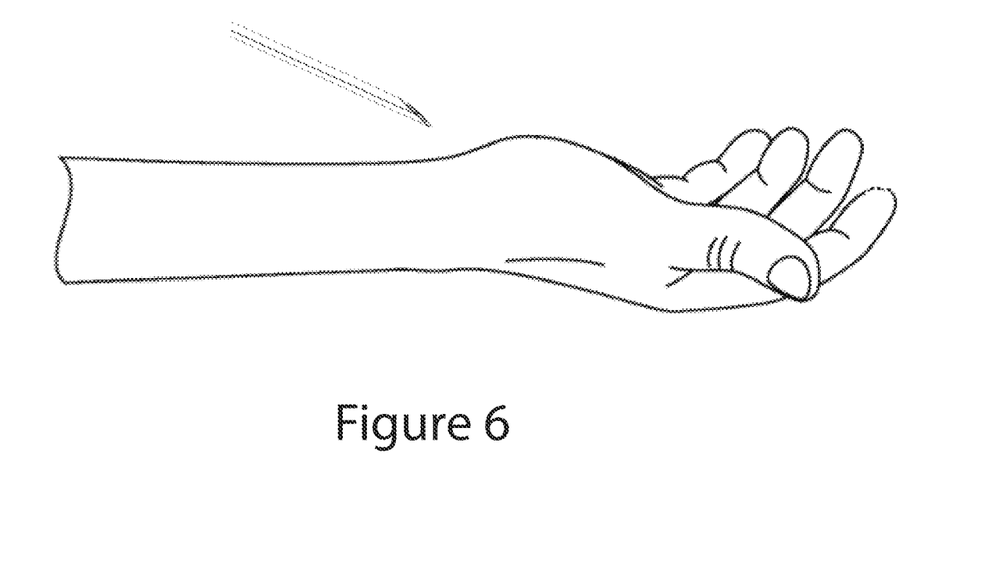
FIG. 6 is an illustration showing a hypodermic needle being inserted into a patient's hand/wrist bevel-up in a proximal-to-distal direction relative to the patient's hand/wrist, wherein the needle is enlarged relative the illustrated hand/wrist for ease of understanding.
Figure 7:
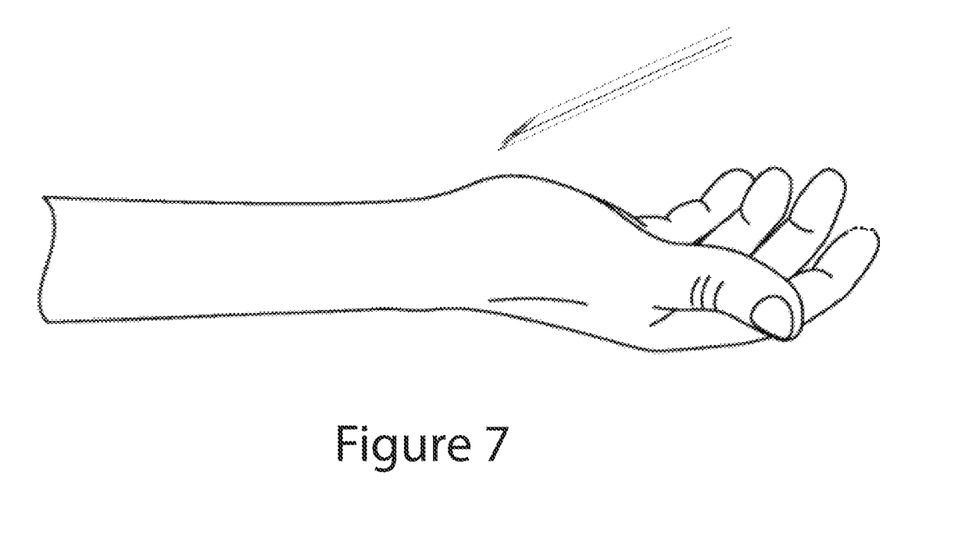
FIG. 7 is an illustration showing a hypodermic needle being inserted into a patient's hand/wrist bevel-up in a distal-to-proximal direction relative to the patient's hand/wrist, wherein the needle is enlarged relative the illustrated hand/wrist for ease of understanding.
Figure 11:
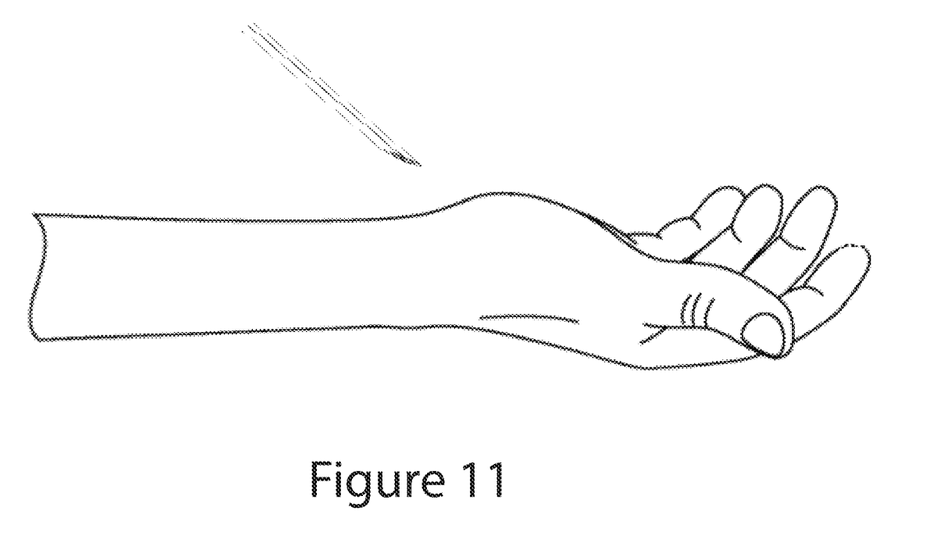
FIG. 11 is an illustration showing a hypodermic needle being inserted into a patient's hand/wrist bevel-down in a proximal-to-distal direction relative to the patient's hand/wrist, wherein the needle is enlarged relative the illustrated hand/wrist for ease of understanding.
Figure 12:
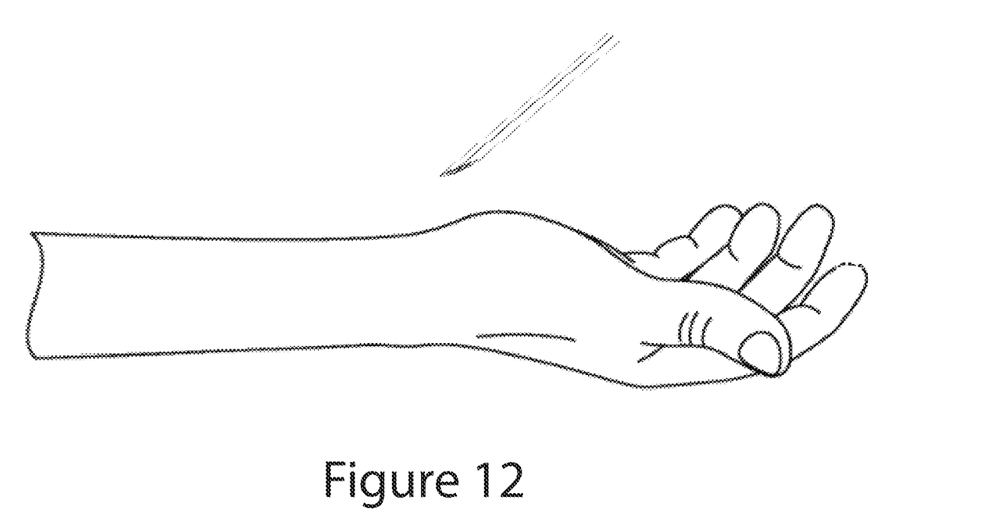
FIG. 12 is an illustration showing a hypodermic needle being inserted into a patient's hand/wrist bevel-down in a distal-to-proximal direction relative to the patient's hand/wrist, wherein the needle is enlarged relative the illustrated hand/wrist for ease of understanding.

The radiologist may introduce the procedure needle through the same entry point used to introduce the numbing needle. As such, the procedure needle is introduced through a wrist crease of the affected wrist in one or more embodiments. Similar to the numbing needle, the procedure needle can be introduced into the patient generally in the proximal-to-distal direction (see FIG. 6) or generally in the distal-to-proximal direction (see FIG. 7). The procedure needle is introduced such that the point 26 of the sharpened distal tip 20 is the first portion of the hypodermic needle introduced into the patient. As discussed above with regard to the numbing needle, the procedure needle may be introduced into the patient at an angle perpendicular to the skin surface. The radiologist, however, will likely introduce the procedure needle at an angle acute to the skin surface. The procedure needle may be oriented in a bevel up orientation (as shown in FIGS. 6-7) or a bevel down orientation (as shown in FIGS. 11-12), depending upon radiologist preference and/or the circumstances associated with the affected wrist. Throughout the interventional radiology procedure, a portion of the shaft 12 of the procedure needle, which extends proximally from the sharpened distal tip 20, will be positioned at an extracorporeal location.

Under continuous ultrasonographic guidance, the procedure needle is guided along the anesthetized track until the point 26 of the sharpened distal tip 20 is immediately superficial of the TCL. In an embodiment, as the radiologist is advancing the procedure needle along the anesthetized track, fluid is at least intermittently injected through the hypodermic needle bore. Intermittently injecting fluid helps the radiologist better identify the exact positioning of the procedure needle relative to various anatomic structures within the patient's body. Depending upon the circumstances, the fluid could be, for example, saline. Alternatively, the fluid may be a numbing fluid containing, for example, a mixture of saline, lidocaine, and triamcinolone acetonide. Intermittently injecting fluid containing a local anesthetic provides the additional benefit of ensuring the patient remains numb throughout the procedure.

Figure 13:
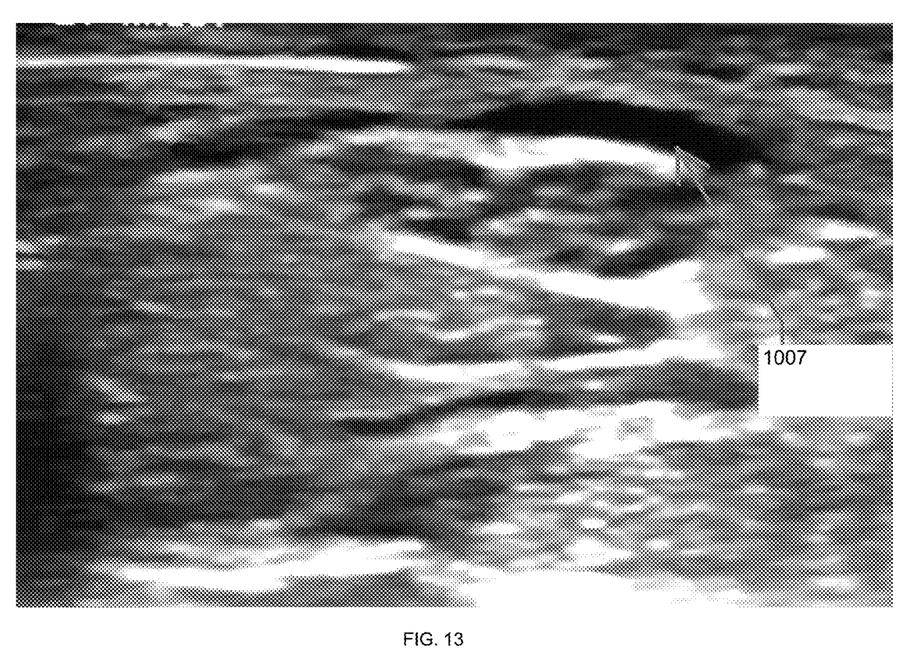
FIG. 13 is an ultrasound image of a carpal tunnel after a fluid pocket is formed between a TCL and a median nerve.

After positioning the procedure needle such that the point 26 of the sharpened distal tip 20 is immediately superficial of the TCL, the radiologist subsequently advances the procedure needle in a deep direction while injecting fluid through the hypodermic needle bore 14. This results in hydrodissection as the sharpened distal tip 20 pierces the TCL. The jet of fluid expelled from the procedure needle separates the median nerve from the deep surface of the TCL. Continued injection of fluid after piercing the TCL forcibly pushes the median nerve away from the TCL (e.g., by the pressure of the injected fluid acting against the median nerve) and provides a fluid pocket 1007 that isolates the median nerve, as shown in FIG. 13. The fluid pocket provides the radiologist enough space to release the TCL during the interventional radiology procedure without contacting and/or damaging the median nerve. In one or more embodiments, the fluid pocket is free of solid blocking structure (e.g., structure other than the distal end portion of the shaft of the needle) between the TCL and the median nerve. For example, no solid blocking structure is intentionally introduced to the fluid pocket to form a guard between the needle and the median nerve in certain embodiments. Rather, in these embodiments, the fluid pocket is used to provide ample clearance for the radiologist to conduct a TCL dissection under ultrasound guidance without substantial risk of damaging the median nerve. For instance, the fluid pocket forms a gap between the TCL and the median nerve of from about 1.0 mm to about 2.0 mm in one or more embodiments. The fluid pocket can be maintained throughout the remaining aspects of the interventional radiology procedure by injecting additional fluid through the procedure needle, as necessary.

After moving the median nerve away from the deep surface of the TCL, the radiologist can proceed to safely dissect the TCL without damaging the median nerve. In one or more embodiments, the radiologist dissects the TCL by sliding a cutting edge associated with the procedure needle along the TCL. This allows the radiologist to perform the dissection from the same entry point that was used to move the median nerve away from the deep surface of the TCL. As will be explained in further detail below, in certain embodiments the cutting edge that is used to dissect the TCL is defined by a portion of the needle itself (e.g., a bevel edge of the needle). It is also contemplated that other cutting edges associated with the needle could be used to perform the dissection. For example, it is expressly contemplated that a cutting implement comprising a cutting edge could be introduced or otherwise extended through the needle bore of the procedure needle and used to dissect the TCL.

In one embodiment, the bevel of the needle is used to dissect the TCL. After using fluid passed through the procedure needle to create the fluid pocket and moving the median nerve away from the TCL, the radiologist rotates the procedure needle approximately 180 degrees or otherwise orients the needle such that the outer bevel edge 30 of the sharpened distal tip 20 contacts the deep surface of the TCL. The ultrasonographic guidance provided by the transducer enables the radiologist to readily identify that the procedure needle has been properly rotated such that the outer bevel edge 30 of the sharpened distal tip 20 is in contact with the TCL. The radiologist may then move the procedure needle in a reciprocating motion while urging the outer bevel edge 30 toward the TCL in a direction transverse to the longitudinal axis LA of the procedure needle. The reciprocating motion causes the outer bevel edge 30 of the sharpened distal tip to wear against the TCL until the TCL is dissected. In this manner, the outer bevel edge 30 functions as a cutting edge sliding along the TCL. Dissection of the TCL releases compression of the median nerve. While dissecting the TCL, the radiologist may intermittently inject fluid. Injection of fluid assists with the dissection because the jet of fluid expelled from the distal needle end 18 of the procedure needle helps force severance of the TCL. In many instances, the TCL has thickened such that it is taut about the median nerve. Thus, the combination of the outer bevel edge 30 of the sharpened distal tip 20 repeatedly wearing against the TCL and the jet of fluid expelled from the distal needle end 18 will provide enough force to sever the taut TCL and release the median nerve. Injection of fluid while dissecting the TCL also enables the radiologist to identify when the TCL has been dissected. After the TCL has been severed, fluid being expelled from the procedure needle will cause the TCL to flutter. This fluttering of the TCL provides the radiologist visual indication via ultrasonic guidance that the TCL has been cut and the median nerve released.

The radiologist may then remove the syringe connected with the fluid fitting and replace the syringe with a second syringe containing a steroid fluid. The steroid fluid could be, for example, a corticosteroid such as triamcinolone acetonide. The second syringe is connected to the fluid fitting such that the fluid fitting (and therefore the procedure needle) is fluidly connected with the steroid fluid. The radiologist may then inject the steroid fluid into the patient at the localized area where the TCL was dissected. Because the affected wrist was not "opened" as is the case in open surgery, the steroid fluid can be readily absorbed by the soft tissue of the patient. Injection of the steroid fluid helps prevent or lessen the inflammatory response of the patient as a result of the dissected TCL. This hinders the potential development of post procedural fibrosis or scar formation. Directing the steroid fluid through the procedure needle, rather than a new hypodermic needle inserted into the patient, ensures the steroid fluid is directed to the localized area where the TCL was dissected. In some instances, scarring of the TCL can result in the reoccurrence of carpal tunnel syndrome. The radiologist may then remove the second syringe from the fluid fitting and replace the second syringe with another syringe containing a non-steroid fluid (e.g., flushing fluid such as lidocaine or saline). This syringe, which is fluidly connected with the fluid fitting, enables the radiologist to flush the procedure needle of any steroid fluid before bringing the procedure needle superficially to the patient's skin. Bringing steroid fluid superficially to the patient's skin can, in some instances, result in skin irritation. After flushing the hypodermic needle, the radiologist may remove the procedure needle from the patient and place a small bandage at the point of entry, if necessary.

Using the interventional radiology procedure described above to dissect the TCL provides for a minimally invasive carpal tunnel release. While multiple entry points may be used throughout the entirety of the procedure (e.g., numbing needle may have a different entry point than the procedure needle), access for dissecting the TCL (or for both moving the median nerve and dissecting the TCL) can be provided through one, and only one, entry point in the hand/wrist of the patient. Unlike open carpal tunnel release in which the entry point is an incision that is in some instances multiple centimeters or inches in length, or even certain less invasive carpal tunnel release procedures that use smaller incisions on the order of 4 mm or greater, the entry point for dissecting the TCL in the procedure described herein is only a hypodermic needle puncture. Thus, in one or more embodiments, the entry point (e.g., hypodermic needle puncture) for an instrument which dissects a TCL has a maximum transverse dimension of less than 3.5 mm, less than 3.0 mm, less than 2.5 mm, less than 2.0 mm, less than 1.7 mm, less than 1.5 mm, or less than 1.4 mm. The small transverse dimension of the entry point facilitates conducting a carpal tunnel release procedure in a minimally invasive manner. The minimally invasive nature helps reduce the risk of infection, enables the procedure to be performed during an office visit at an outpatient facility (which helps reduce medical costs), drastically minimizes recovery time necessary for the entry point to heal, and significantly reduces the risk of scarring (both on the skin surface and internally at the location where the TCL is dissected).

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method of performing an interventional radiology procedure on a patient exhibiting symptoms of carpal tunnel syndrome in an affected wrist, the method comprising:
    orienting the affected wrist of the patient in a palmar position;
    guiding a hypodermic needle through a wrist crease of the affected wrist to a position immediately superficial of the transverse carpal ligament (TCL), the hypodermic needle having a hypodermic needle bore and a sharpened distal tip, wherein fluid is at least intermittently injected through the hypodermic needle bore while the hypodermic needle is guided to the position immediately superficial of the TCL;
    piercing the sharpened distal tip of the hypodermic needle through the TCL while injecting fluid, the fluid pushing the median nerve away from the TCL and providing a fluid pocket, the fluid pocket isolating the median nerve;
    orienting the hypodermic needle such that at least a portion of the sharpened distal tip is in contact with the TCL; and
    dissecting the TCL with the sharpened distal tip by moving the hypodermic needle in a reciprocating motion, the reciprocating motion causing the sharpened distal tip to wear against the TCL until said TCL is dissected;
    wherein the interventional radiology procedure is performed under continuous imaging, thereby enabling anatomic structures of the affected wrist to be visualized throughout the procedure.

2. The method of claim 1, wherein the sharpened distal tip comprises at least one bevel, the bevel having an inner bevel edge and an outer bevel edge, the inner bevel edge at least partially defining the hypodermic needle bore, wherein the method further comprises:
    orienting the hypodermic needle such that (i) the outer bevel edge contacts the TCL and (ii) the inner bevel edge is spaced from the TCL; and
    dissecting the TCL with the sharpened distal tip by moving the hypodermic needle in a reciprocating motion, the reciprocating motion causing the outer bevel edge to wear against the TCL until said TCL is dissected.

3. The method of claim 2, wherein the method further comprises:
    intermittently injecting fluid through the hypodermic needle bore while dissecting the TCL, the fluid ensuring that the median nerve remains isolated by the fluid pocket throughout the dissection step.

4. The method of claim 2, wherein the method further comprises:

placing an ultrasound transducer on a palmar side of the affected wrist, the ultrasound transducer enabling a radiologist to maintain continuous imaging throughout the procedure.

5. A method of performing an image guided carpal tunnel release procedure, the method comprising:

directing fluid through a hypodermic needle toward a median nerve of a patient to move the median nerve away from a deep surface of a transverse carpal ligament (TCL) of the patient; and subsequently dissecting the TCL with the hypodermic needle by sliding a cutting edge associated with the hypodermic needle along the TCL; wherein access for said dissecting the TCL is provided through one, and only one, entry point in the hand or wrist of the patient, the entry point having a transverse dimension of less than 3.5 mm; wherein the entry point consist of a hypodermic needle puncture; and wherein an ultrasound transducer is held in one hand and an instrument comprising the hypodermic needle is held in an opposite hand while directing fluid through the hypodermic needle toward the median nerve.

6. The method of claim 5, wherein the hypodermic needle puncture has a maximum transverse dimension of less than 3.0 mm.

7. The method of claim 6, wherein the hypodermic needle puncture has a maximum transverse dimension of less than 2.5 mm.

8. The method of claim 7, wherein the hypodermic needle puncture has a maximum transverse dimension of less than 2.0 mm.

9. The method of claim 8, wherein the hypodermic needle puncture has a maximum transverse dimension of less than 1.7 mm.

10. The method of claim 5, wherein sliding the cutting edge along the TCL comprises reciprocating the cutting edge along the TCL.

11. The method of claim 5, wherein the hypodermic needle has a longitudinal axis.

12. The method of claim 11 wherein said engaging the cutting edge with the TCL comprises urging the cutting edge toward the TCL in a direction transverse to the longitudinal axis.

13. The method of claim 11, wherein the hypodermic needle comprises a rigid shaft extending longitudinally along the longitudinal axis.

14. The method of claim 13, wherein a portion of rigid shaft extends proximally from the cutting edge to an extra-corporeal location as the TCL is dissected.

15. The method of claim 5, further comprising urging the cutting edge toward the TCL in a direction transverse to the longitudinal axis while sliding the cutting edge along the TCL.

16. The method of claim 5, wherein the cutting edge comprises an edge of a bevel of the hypodermic needle.

17. The method of claim 5, wherein the image guided carpal tunnel release procedure is performed using ultrasound imaging.

18. The method of claim 5, wherein an ultrasound transducer is held in one hand and holds an instrument comprising the hypodermic needle in an opposite hand while dissecting the TCL.

19. The method of claim 5, wherein said directing fluid through the hypodermic needle toward the median nerve creates a fluid pocket between the TCL and the median nerve.

20. The method of claim 19, wherein the fluid pocket is generally maintained as the TCL is dissected.

21. The method of claim 20, wherein the fluid pocket is free of solid blocking structure between the TCL and the median nerve as the TCL is dissected.

22. The method of claim 5, further comprising directing fluid through the hypodermic needle while sliding the cutting edge along the TCL.

23. The method of claim 5, wherein the cutting edge extends along an axis of the hypodermic needle.

24. The method of claim 23, wherein the cutting edge extend at an angle with respect to the axis of the needle of less than 45°.

* * * * *